United States Patent
Sakuragi (10) Patent No.: US 11,607,273 B2
(45) Date of Patent: Mar. 21, 2023

(54) VIRTUAL STENT PLACEMENT APPARATUS, VIRTUAL STENT PLACEMENT METHOD, AND VIRTUAL STENT PLACEMENT PROGRAM

(71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 167 days.

(21) Appl. No.: 16/780,913

(22) Filed: Feb. 4, 2020

(65) Prior Publication Data

US 2020/0170713 A1 Jun. 4, 2020

Related U.S. Application Data

(63) Continuation of application No. PCT/JP2018/025284, filed on Jul. 3, 2018.

(30) Foreign Application Priority Data

Sep. 27, 2017 (JP) .............................. JP2017-185646

(51) Int. Cl.
| | |
|---|---|
| G06G 7/48 | (2006.01) |
| A61B 34/10 | (2016.01) |
| A61F 2/95 | (2013.01) |
| A61B 90/00 | (2016.01) |

(52) U.S. Cl.
CPC ................ *A61B 34/10* (2016.02); *A61F 2/95* (2013.01); *A61B 2034/102* (2016.02); *A61B 2090/374* (2016.02); *A61B 2090/3762* (2016.02)

(58) Field of Classification Search
CPC .............. A61B 34/10; A61B 2034/102; A61B 2090/374; A61B 2090/3762; A61B 6/03; A61B 2034/101; A61B 2034/105; A61F 2/95; A61F 2/07; G06T 2207/30021; G06T 2207/30101; G06T 2207/30172; G06T 7/12; G06T 7/13; G06T 7/73
See application file for complete search history.

(56) References Cited

U.S. PATENT DOCUMENTS

| 6,096,073 A * | 8/2000 | Webster .................. A61F 2/915 623/1.16 |
| 2002/0068968 A1 * | 6/2002 | Hupp ........................ A61F 2/90 623/1.15 |

(Continued)

FOREIGN PATENT DOCUMENTS

| JP | 2001079097 | 3/2001 |
| JP | 2003245360 | 9/2003 |

OTHER PUBLICATIONS

Murasato, Yoshinobu, et al. "Optimal kissing balloon inflation after single-stent deployment in a coronary bifurcation model." EuroIntervention 10.8 (2014): 934-941.*

(Continued)

*Primary Examiner* — Rehana Perveen
*Assistant Examiner* — Nithya J. Moll
(74) *Attorney, Agent, or Firm* — JCIPRNET (57) ABSTRACT

A virtual stent placement apparatus, a virtual stent placement method, and a virtual stent placement program for preventing a stent from blocking a branch of a blood vessel in a case in which the stent is virtually placed in the blood vessel extracted from a medical image are disclosed.

8 Claims, 9 Drawing Sheets

(56) References Cited

U.S. PATENT DOCUMENTS

| 2007/0135707 | A1* | 6/2007 | Redel | A61B 6/504 |
| | | | | 600/424 |
| 2008/0177367 | A1* | 7/2008 | Stys | A61F 2/90 |
| | | | | 623/1.11 |
| 2009/0088830 | A1* | 4/2009 | Mohamed | A61F 2/91 |
| | | | | 623/1.11 |
| 2010/0094401 | A1 | 4/2010 | Kolbel et al. | |
| 2012/0123526 | A1 | 5/2012 | Ko et al. | |
| 2018/0085170 | A1* | 3/2018 | Gopinath | A61B 8/466 |

OTHER PUBLICATIONS

Demanget, Nicolas, et al. "Computational comparison of the bending behavior of aortic stent-grafts." Journal of the mechanical behavior of biomedical materials 5.1 (2012): 272-282.*

Kaladji, Adrien, et al. "Centerline is not as accurate as outer curvature length to estimate thoracic endograft length." European Journal of Vascular and Endovascular Surgery 46.1 (2013): 82-86.*

Office Action of Japan Counterpart Application, with English translation thereof, dated Oct. 27, 2020, pp. 1-5.

"International Search Report (Form PCT/ISA/210) of PCT/JP2018/025284," dated Sep. 25, 2018, with English translation thereof, pp. 1-3.

"Written Opinion of the International Searching Authority (Form PCT/ISA/237) of PCT/JP2018/025284," dated Sep. 25, 2018, with English translation thereof, pp. 1-9.

Office Action of Japan Counterpart Application, with English translation thereof, dated Aug. 11, 2020, pp. 1-5.

* cited by examiner

VIRTUAL STENT PLACEMENT APPARATUS, VIRTUAL STENT PLACEMENT METHOD, AND VIRTUAL STENT PLACEMENT PROGRAM

CROSS-REFERENCE TO RELATED APPLICATIONS

This application is a Continuation of PCT International Application No. PCT/JP 2018/025284 filed on Jul. 3, 2018, which claims priority under 35 U. S. C § 119(a) to Japanese Patent Application No. 2017-185646 filed on Sep. 27, 2017. Each of the above application(s) is hereby expressly incorporated by reference, in its entirety, into the present application.

BACKGROUND OF THE INVENTION

1. Field of the Invention

The present invention relates to a virtual stent placement apparatus, a virtual stent placement method, and a virtual stent placement program for placing a virtual stent in a blood vessel region extracted from a medical image such as a computed radiography (CT) image.

2. Description of the Related Art

In recent years, as a treatment for an aneurysm or the like, a surgical operation has been performed which places a stent in the artery. In addition, before a surgical operation, an artery region is extracted from a medical image, such as a CT image of a patient, and a simulation in which a stent is virtually placed in the extracted artery region is performed to check the size of the stent to be actually placed in advance.

In order to virtually place a stent, generally, a core line of the blood vessel is extracted from the blood vessel, such the extracted artery, and a virtual stent having a specific length is placed along the core line. However, in an extremely curved blood vessel, such as an aortic arch, for example, the length of the outer side (that is, the large curvature side) of the curvature of the blood vessel is larger than the length of the core line. For this reason, in a case in which the virtual stent is placed in the curved blood vessel on the basis of the core line and the size of the stent is determined, there is a problem that the length of the stent on the large curvature side of the blood vessel is insufficient in the actual placement of the stent in the patient.

Therefore, the maximum contour length of the large curvature side of the virtual stent is calculated (see JP2001-079097A). The technique described in JP2001-079097A extracts a blood vessel from a CT image, generates a stent graft model on the basis of a core line of the blood vessel and a plurality of rings perpendicular to the core line, and designs a stent. In this case, the large-arm-side maximum contour length of the virtual stent is calculated by setting the interval at which the rings are placed, the number of rings, and the radius of the rings.

The use of the technique described in JP2001-079097A makes it possible to know the maximum contour length of the stent in advance. Therefore, in a case in which the stent is actually placed in the patient, it is possible to solve the problem that the length of the stent is insufficient on the large curvature side of the blood vessel.

SUMMARY OF THE INVENTION

As described above, in a case in which the stent is virtually placed, the cross sections of both ends of the virtual stent are set as cross sections perpendicular to the core line. On the other hand, in a case in which the stent is actually placed in the blood vessel, it is necessary to adjust the direction of the cross section such that the stent does not block a branch of the blood vessel in the vicinity of both ends of the stent. Therefore, even in a case in which the stent is virtually placed, it is desirable that the stent does not block the branch of the blood vessel.

The invention has been made in view of the above-mentioned problems and an object of the invention is to provide a technique that prevents a stent from blocking a branch of a blood vessel in a case in which the stent is virtually placed in the blood vessel extracted from a medical image.

According to the invention, there is provided a virtual stent placement apparatus comprising: an extraction unit that extracts a blood vessel region and a core line of the blood vessel region from a medical image; an information acquisition unit that acquires information of a diameter of a virtual stent which is placed in the blood vessel region and start and end positions in a case in which the virtual stent is placed; a placement unit that places the virtual stent in the blood vessel region; and an inclination change unit that changes an inclination of stent cross sections which are cross sections of the placed virtual stent at the start position and the end position with respect to cross sections perpendicular to the core line.

In the virtual stent placement apparatus according to the invention, the information acquisition unit may estimate the diameter of the virtual stent from the blood vessel region.

In the virtual stent placement apparatus according to the invention, the inclination change unit may receive a command to change the inclination of the stent cross section and change the inclination of the stent cross section with respect to the cross section perpendicular to the core line.

In the virtual stent placement apparatus according to the invention, the inclination change unit may change the inclination of the stent cross section with respect to the cross section perpendicular to the core line to avoid an overlap between the stent cross section and a branch of the blood vessel region.

In the virtual stent placement apparatus according to the invention, the extraction unit may extract another core line branched from the core line, and the inclination change unit may change the inclination of the stent cross section until the stent cross section does not overlap the branched core line.

In the virtual stent placement apparatus according to the invention, the inclination change unit may change the inclination of the stent cross section along a maximum contour line of the blood vessel region.

In the virtual stent placement apparatus according to the invention, the placement unit may change a position where the virtual stent is placed with the change in the inclination of the stent cross section.

According to the invention, there is provided a virtual stent placement method comprising: extracting a blood vessel region and a core line of the blood vessel region from a medical image; acquiring information of a diameter of a virtual stent which is placed in the blood vessel region and start and end positions in a case in which the virtual stent is placed; placing the virtual stent in the blood vessel region; and changing an inclination of stent cross sections which are cross sections of the placed virtual stent at the start position and the end position with respect to cross sections perpendicular to the core line.

In addition, a program that causes a computer to perform the virtual stent placement method according to the invention may be provided.

According to the invention, there is provided another virtual stent placement apparatus comprising a memory that stores commands to be executed by a computer and a processor that is configured to execute the stored commands. The processor performs a process of extracting a blood vessel region and a core line of the blood vessel region from a medical image, a process of acquiring information of a diameter of a virtual stent which is placed in the blood vessel region and start and end positions in a case in which the virtual stent is placed, a process of placing the virtual stent in the blood vessel region, and a process of changing an inclination of stent cross sections which are cross sections of the placed virtual stent at the start position and the end position with respect to cross sections perpendicular to the core line.

According to the invention, a blood vessel region is extracted from a medical image and a core line of the blood vessel region is extracted. The information of a diameter of a virtual stent which is placed in the blood vessel region and start and end positions in a case in which the virtual stent is placed is acquired. Then, the virtual stent is placed in the blood vessel region and the inclination of stent cross sections which are cross sections of the placed virtual stent at the start position and the end position with respect to cross sections perpendicular to the core line is changed. Therefore, it is possible to prevent the virtual stent from blocking a branch of the blood vessel by appropriately changing the stent cross section. As a result, in a case in which the stent is actually placed in the blood vessel, it is possible to prevent the stent from blocking the branch of the blood vessel with reference to the position where the virtual stent is placed.

DESCRIPTION OF THE PREFERRED EMBODIMENTS

Figure 1:
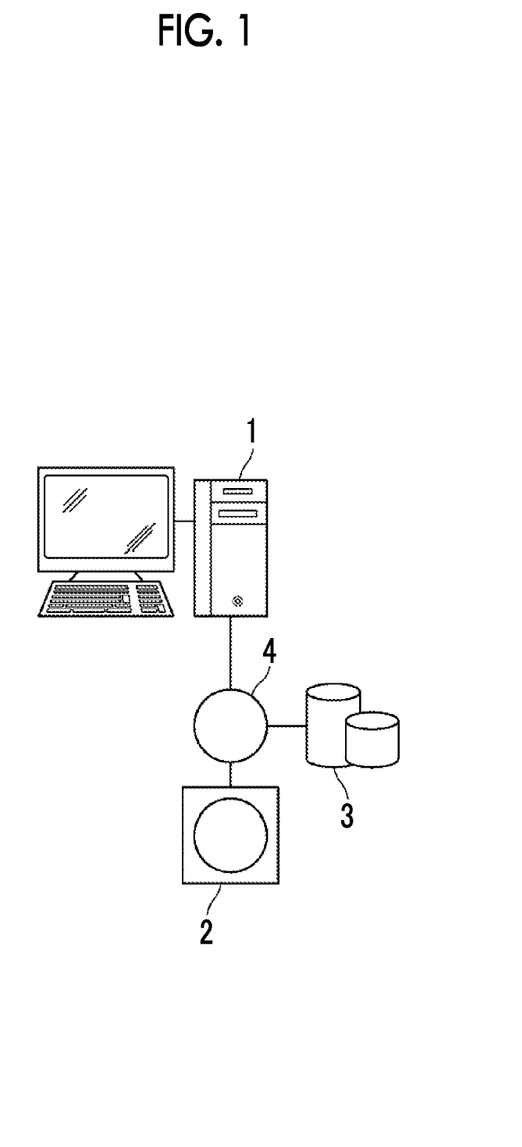
FIG. 1 is a hardware configuration diagram illustrating the outline of a diagnosis support system to which a virtual stent placement apparatus according to an embodiment of the invention is applied.

Hereinafter, an embodiment of the invention will be described with reference to the drawings. FIG. 1 is a hardware configuration diagram illustrating the outline of a diagnosis support system to which a virtual stent placement apparatus according to the embodiment of the invention is applied. As illustrated in FIG. 1, in the diagnosis support system, a virtual stent placement apparatus 1 according to this embodiment, a three-dimensional imaging apparatus 2, and an image storage server 3 are connected through a network 4 so as to communicate with each other. In the diagnosis support system, a three-dimensional image of the aorta of a subject is displayed and a virtual stent is placed in the aorta included in the displayed three-dimensional image as a simulation for correctly placing a stent in the aorta.

The three-dimensional imaging apparatus 2 is an apparatus that captures an image of a diagnosis target part of the subject and generates a three-dimensional image indicating the part. Specifically, the three-dimensional imaging apparatus 2 is, for example, a CT apparatus, a magnetic resonance imaging (MRI) apparatus, or a positron emission tomography (PET) apparatus. A three-dimensional image V0 generated by the three-dimensional imaging apparatus 2 is transmitted to the image storage server 3 and is then stored therein. In this embodiment, since the place in which the virtual stent is placed is the aorta of the subject, the diagnosis target part of the subject is the chest including the aorta. The three-dimensional imaging apparatus 2 is a CT apparatus and generates a three-dimensional image formed by tomographic images of a plurality of axial cross sections for the chest of the subject. The three-dimensional image corresponds to a medical image.

The image storage server 3 is a computer that stores various kinds of data and manages the data and comprises a large-capacity external storage device and database management software. The image storage server 3 communicates with other apparatuses through the wired or wireless network 4 to transmit and receive, for example, image data. Specifically, the image storage server 3 acquires image data, such as the three-dimensional image generated by the three-dimensional imaging apparatus 2, through the network 4, stores the image data in a recording medium, such as a large-capacity external storage device, and manages the image data. The storage format of the image data and the communication between the apparatuses through the network 4 are based on a protocol such as Digital Imaging and Communication in Medicine (DICOM).

The virtual stent placement apparatus 1 is configured by installing a virtual stent placement program according to the invention in one computer. The computer may be a workstation or a personal computer that is directly operated by a doctor who performs diagnosis or may be a server computer that is connected to the computer through the network. An image display program is recorded on a recording medium, such as a digital versatile disc (DVD) or a compact disc read only memory (CD-ROM), is distributed, and is then installed in the computer from the recording medium. Alternatively, the image display program is stored in a storage device of a server computer connected to the network or a network storage such that it can be accessed from the outside, is downloaded to the computer used by the doctor on demand, and is then installed in the computer.

Figure 2:
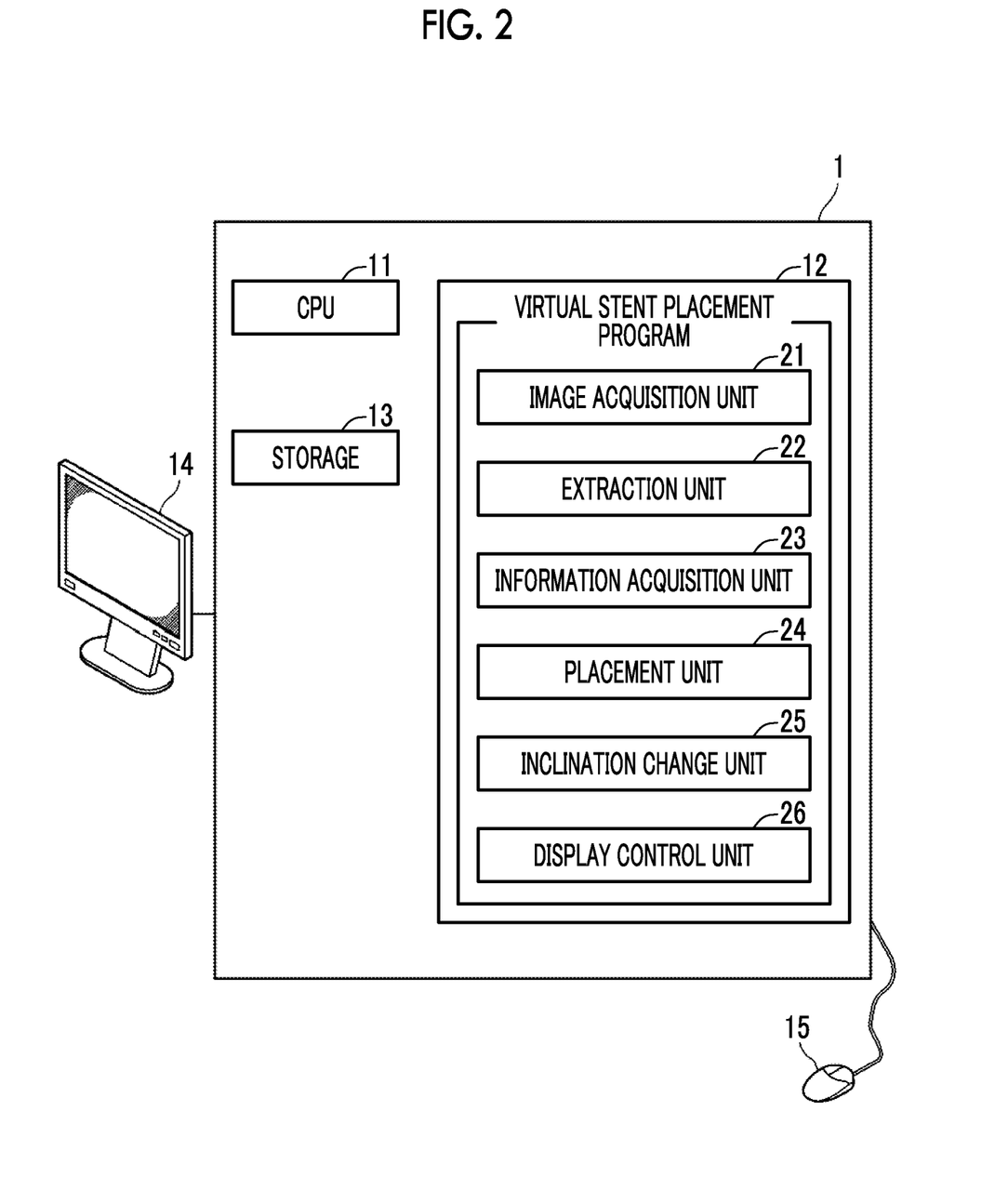
FIG. 2 is a diagram schematically illustrating the configuration of the virtual stent placement apparatus.

FIG. 2 is a diagram schematically illustrating the configuration of the virtual stent placement apparatus 1 implemented by installing the virtual stent placement program in the computer. As illustrated in FIG. 2, the virtual stent placement apparatus 1 comprises a central processing unit (CPU) 11, a memory 12, and a storage 13 as the configuration of a standard workstation. In addition, a display 14, such as a liquid crystal display, and an input unit 15, such as a mouse or a keyboard, are connected to the virtual stent placement apparatus 1.

The storage 13 is a storage device such as a hard disk drive or a solid state drive (SSD). The storage 13 stores various kinds of information including the three-dimensional image V0 of the subject acquired from the image storage server 3 through the network 4 and information required for processes.

The memory 12 stores the virtual stent placement program. The virtual stent placement program defines, as the processes performed by the CPU 11, an image acquisition process that acquires the three-dimensional image V0, an extraction process that extracts a blood vessel region and a core line of the blood vessel region from the three-dimensional image V0, an information acquisition process that acquires information of the diameter of the virtual stent placed in the blood vessel region and start and end positions in a case in which the virtual stent is placed, a placement process that places the virtual stent in the blood vessel region, an inclination change process that changes the inclination of stent cross sections which are the cross sections of the placed virtual stent at the start position and the end position with respect to cross sections perpendicular to the core line, and a display control process that displays, for example, the three-dimensional image V0.

The CPU 11 performs these processes according to the program such that the computer functions as an image acquisition unit 21, an extraction unit 22, an information acquisition unit 23, a placement unit 24, an inclination change unit 25, and a display control unit 26. In this embodiment, the functions of each unit are implemented by the virtual stent placement program. However, the invention is not limited thereto. For example, a plurality of integrated circuits (IC), a processor, an application specific integrated circuit (ASIC), a field-programmable gate array (FPGA), and a memory may be appropriately combined to implement the functions of each unit.

The image acquisition unit 21 acquires the three-dimensional image V0 of the chest of the subject for placing the virtual stent from the image storage server 3. In a case in which the three-dimensional image V0 has already been stored in the storage 13, the image acquisition unit 21 may acquire the three-dimensional image V0 from the storage 13.

The extraction unit 22 extracts an aorta region as the blood vessel region from the three-dimensional image V0 using, for example, the method disclosed in JP2010-200925A and JP2010-220742A. In this method, first, the positions and main axis directions of a plurality of candidate points forming a core line of the aorta are calculated on the basis of the value of voxel data forming the three-dimensional image V0. Alternatively, the Hessian matrix for the three-dimensional image V0 is calculated and the eigenvalue of the calculated Hessian matrix is analyzed to calculate the positional information and main axis direction of a plurality of candidate points forming the core line of the aorta. Then, a feature amount indicating the blood vessel, particularly, the aortic characteristics are calculated for voxel data around the candidate point and it is determined whether or not the voxel data indicates the aorta on the basis of the calculated feature amount. The determination based on the feature amount is performed on the basis of an evaluation function which has been acquired in advance by machine learning. In this way, the blood vessel region, that is, the aorta region and the core line thereof are extracted from the three-dimensional image V0. The core line may be extracted by extracting the blood vessel region first and performing a thinning process for the blood vessel region.

Figure 3:
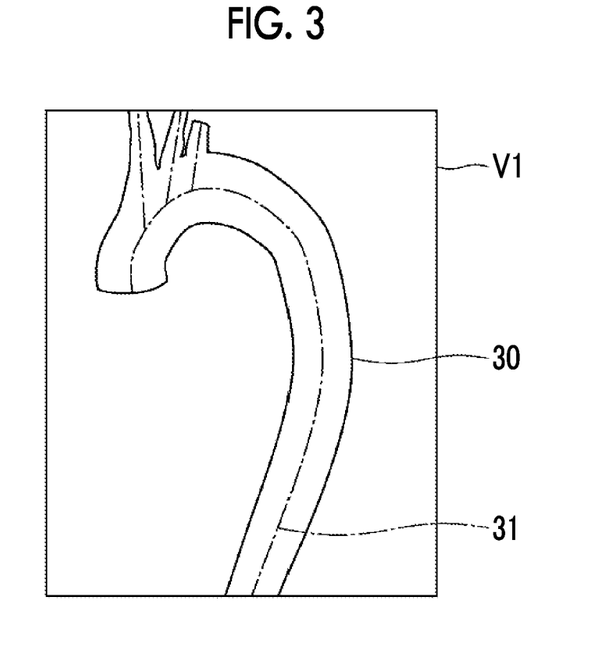
FIG. 3 is a diagram illustrating a three-dimensional image of a blood vessel region displayed on a display.

The display control unit 26 displays the extracted blood vessel region on the display 14. Since the extracted blood vessel region is a three-dimensional image, the display control unit 26 displays the three-dimensional image of the blood vessel region on the display 14 using a predetermined display method. Examples of the display method include projection methods, such as a maximum intensity projection (MIP) method and a minimum intensity projection (MinIP) method, and a volume rendering (VR) method. The three-dimensional image of the blood vessel region displayed on the display 14 is illustrated in FIG. 3. As illustrated in FIG. 3, a three-dimensional image V1 of a blood vessel region 30 is displayed on the display 14. A core line 31 of the blood vessel region 30 is also displayed in the three-dimensional image V1.

The information acquisition unit 23 acquires the information of the diameter of the virtual stent placed in the blood vessel region and the start and end positions in a case in which the virtual stent is placed. In this embodiment, the diameter of the virtual stent is acquired in response to an input from the operator through the input unit 15. Further, the information acquisition unit 23 acquires the information of the start and end positions of the virtual stent input by the operator through the input unit 15 with reference to the three-dimensional image V1 of the blood vessel region displayed on the display 14.

Figure 4:
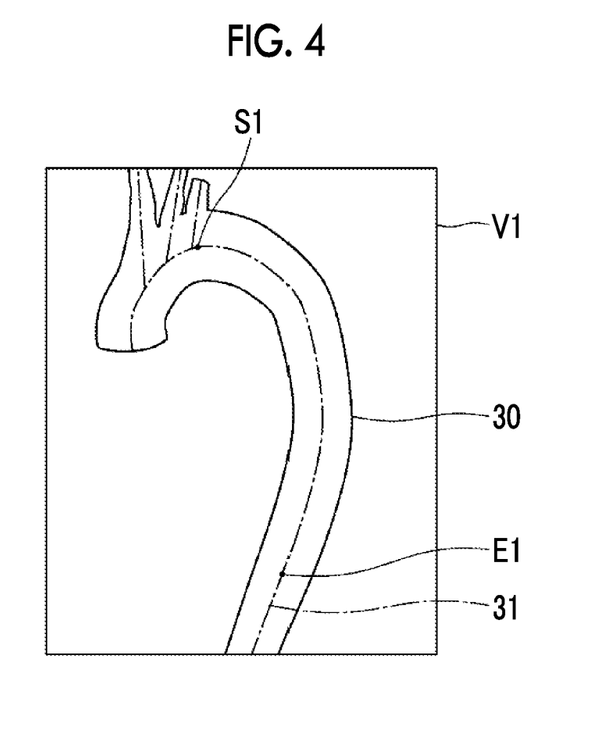
FIG. 4 is a diagram illustrating a three-dimensional image in which a start position and an end position of a virtual stent are designated.

FIG. 4 is a diagram illustrating the three-dimensional image V1 in which a start position S1 and an end position E1 of the virtual stent are designated. In addition, after the start position S1 and the end position E1 of the virtual stent are designated, the diameter of a cross section perpendicular to a core line 31 in the blood vessel region 30 between the start position S1 and the end position E1 may be measured to acquire the information of the diameter of the virtual stent. Further, the area or perimeter of the cross section perpendicular to the core line 31 in the blood vessel region 30 between the start position S1 and the end position E1 may be measured and the information of the diameter of the virtual stent may be calculated from the measured area or perimeter. In a case in which the diameter of the blood vessel region 30 is measured, the measurement may be performed at only one position between the start position S1 and the end position E1 or may be performed at a plurality of positions. In a case in which the diameter is measured at only one position, for example, the diameter at the midpoint between the start position S1 and the end position E1 may be measured and used as the information of the diameter of the virtual stent. In a case in which the diameter is measured at a plurality of positions, a representative value, such as the average value or intermediate value of the diameters at the plurality of positions, may be used as the information of the diameter of the virtual stent. That is, the information acquisition unit 23 may estimate the diameter of the virtual stent from the blood vessel region.

Figure 5:
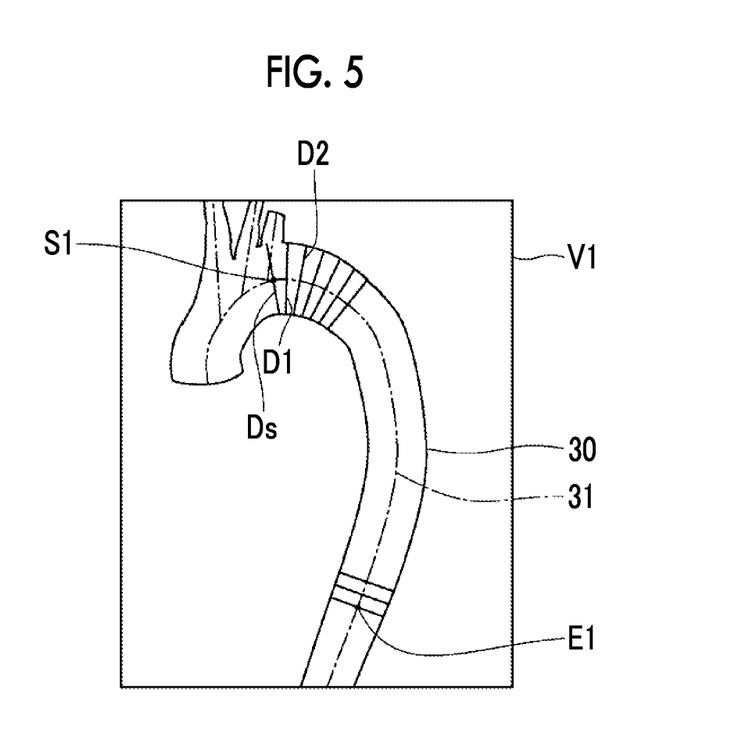
FIG. 5 is a diagram illustrating the determination of a maximum contour line of the blood vessel region.

The information acquisition unit 23 determines a maximum contour line of the blood vessel region 30 between the start position S1 and the end position E1. FIG. 5 is a diagram illustrating the determination of the maximum contour line. As illustrated in FIG. 5, first, the information acquisition unit 23 sets a cross section Ds perpendicular to the core line 31 at the start position S1. Then, a circle having the diameter of the virtual stent is defined in the cross section Ds and contour points of the circle are set on the circumference of the circle at predetermined intervals. Then, cross sections D1, D2, . . . are set at predetermined intervals along the core line 31 toward the end position E1. As in the cross section Ds, circles having the diameter of the virtual stent are defined in the cross sections D1, D2, . . . , and contour points of the circles are set on the circumferences of the circles at predetermined intervals.

Figure 6:
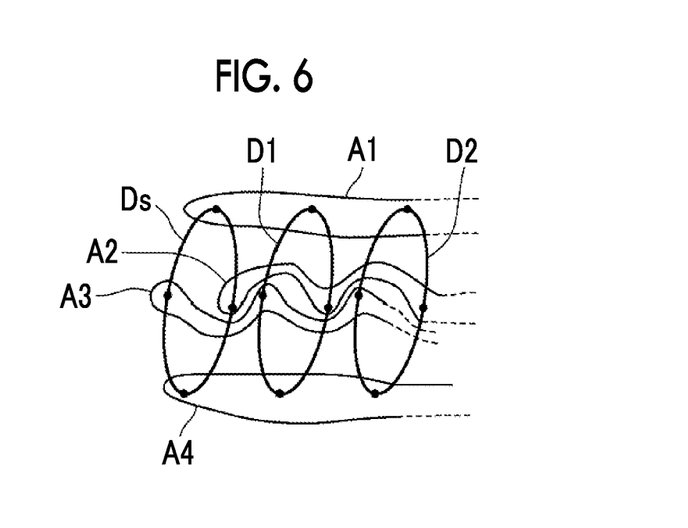
FIG. 6 is a diagram illustrating the setting of a contour point group.

Then, sets of the closest contour points between the contour points in the cross section Ds and the contour points in the cross section D1 adjacent to the cross section Ds are set. This is repeated from the start position S1 to the end position E1 to set contour point groups corresponding to each other on the circumferences corresponding to the cross sections perpendicular to the core line 31 as illustrated in FIG. 6. In FIG. 6, only the cross sections Ds, D1, and D2 are illustrated and the corresponding contour points among the contour points set in the cross sections Ds, D1, and D2 are surrounded by lines A1 to A4. Here, in FIG. 6, four contour points are set on the circumference. However, the invention is not limited thereto. It is preferable to set a larger number of contour points. Then, the information acquisition unit 23 connects the corresponding contour point groups to acquire the contour line groups of the blood vessel region 30 in a direction along the core line 31. In addition, among the acquired contour line groups, a contour line having the maximum length is determined as the maximum contour line. The side on which the maximum contour line exists in the blood vessel region 30, that is, the aorta is a large curvature side.

Figure 7:
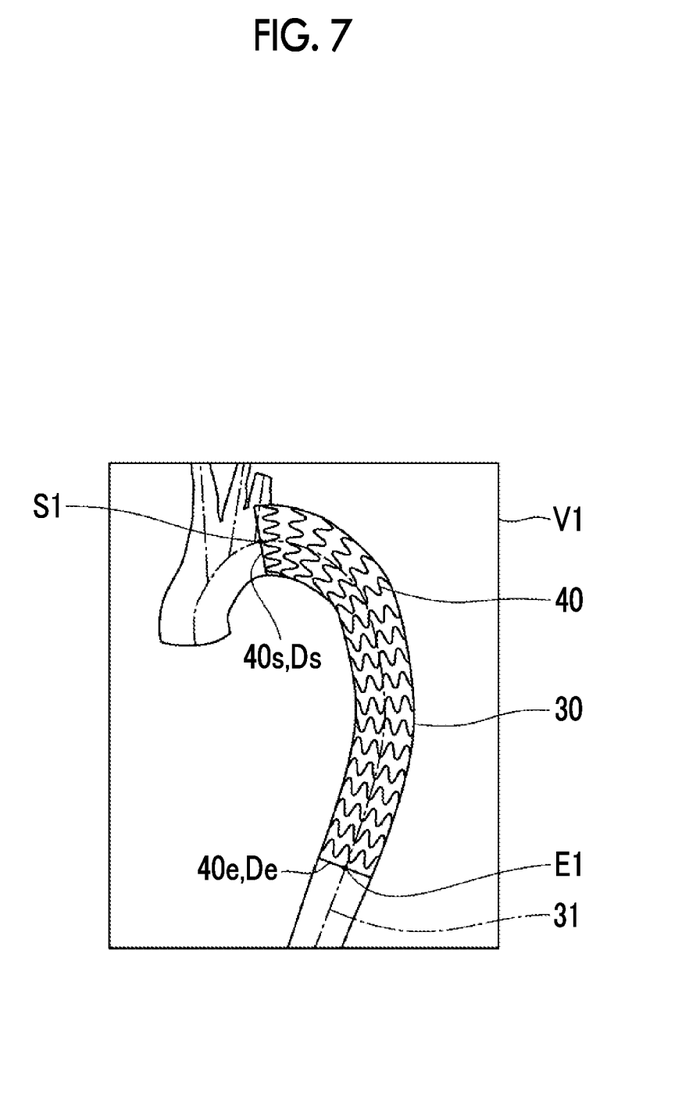
FIG. 7 is a diagram illustrating a three-dimensional image in which the virtual stent is placed.

The placement unit 24 places the virtual stent in the blood vessel region 30. The virtual stent to be placed has the diameter based on the information acquired by the information acquisition unit 23 and has a length between the start position S1 and the end position E1. The placement unit 24 places the virtual stent in the blood vessel region 30 on the basis of the information acquired by the information acquisition unit 23. FIG. 7 is a diagram illustrating the three-dimensional image V1 in which a virtual stent 40 is placed. As illustrated in FIG. 7, in the three-dimensional image V1, the virtual stent 40 is placed between the start position S1 and the end position E1 set on the core line 31 of the blood vessel region 30. FIG. 7 also illustrates a mesh pattern forming the stent. As illustrated in FIG. 7, a stent cross section 40s of the virtual stent 40 at the start position S1 is matched with the cross section Ds perpendicular to the core line 31 at the start position S1. Further, a stent cross section 40e of the virtual stent 40 at the end position E1 is matched with the cross section De perpendicular to the core line 31 at the end position E1.

Here, in a case in which the stent is actually placed in the blood vessel, it is necessary to adjust the direction of the stent cross section so as not to block a branch of the blood vessel in the vicinity of both ends of the stent.

Figure 8:
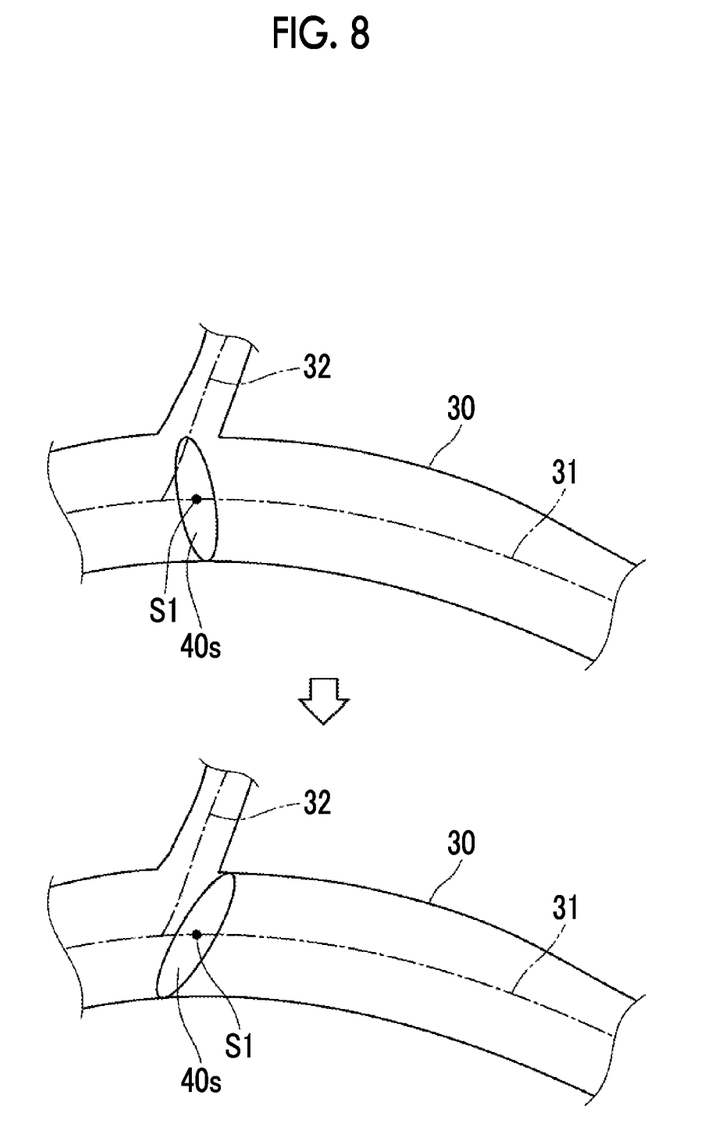
FIG. 8 is a diagram illustrating a change in the inclination of a stent cross section.

The inclination change unit 25 changes the inclination of the stent cross sections 40s and 40e which are the cross sections of the placed virtual stent 40 at the start position S1 and the end position E1 with respect to the cross sections Ds and De perpendicular to the core line 31. Specifically, the inclination change unit 25 changes the inclination of the stent cross sections 40s and 40e with respect to the cross sections Ds and De perpendicular to the core line 31 to avoid the overlap between the stent cross sections 40s and 40e and the branches of the blood vessel region 30. In order to avoid the overlap, the inclination change unit 25 determines whether or not each of the stent cross section 40s of the virtual stent 40 at the start position S1 and the stent cross section 40e of the virtual stent 40 at the end position E1 overlaps the branch of the blood vessel region 30. FIG. 8 is a diagram illustrating a change in the inclination of the cross section. In FIG. 8, the virtual stent 40 is not illustrated. As illustrated in the upper diagram of FIG. 8, it is assumed that the stent cross section 40s of the virtual stent 40 at the start position S1 overlaps a branch of the blood vessel region 30. Here, the determination of whether or not the stent cross section 40s overlaps the branch may be performed by determining whether or not the stent cross section 40s overlaps a core line 32 branched from the core line 31. The core line 32 is "another core line branched from the core line".

Figure 9:
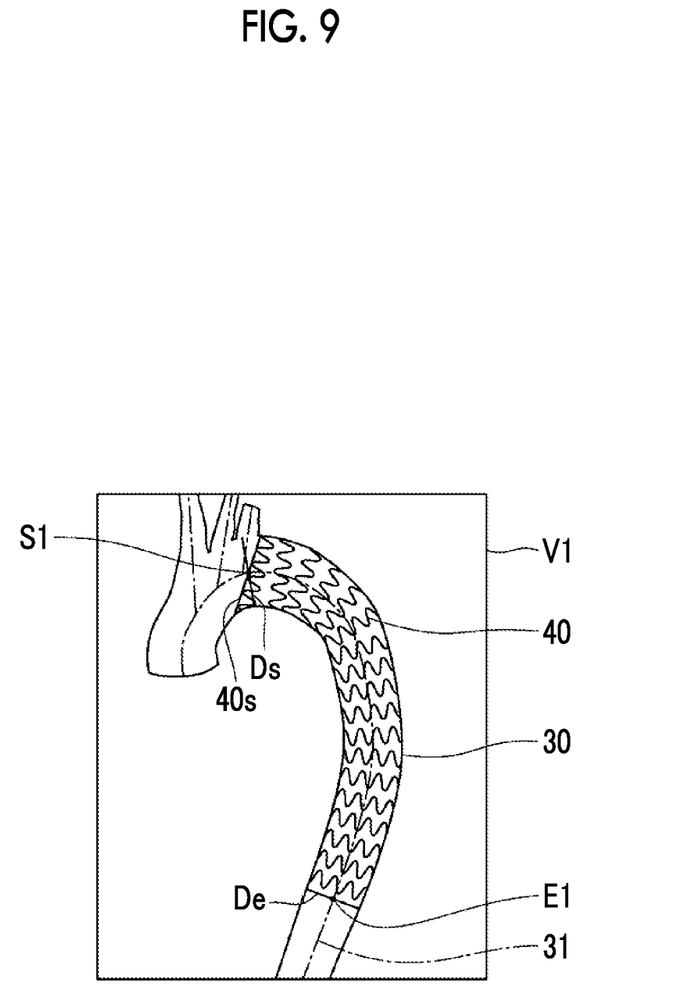
FIG. 9 is a diagram illustrating a state in which the inclination of a cross section is changed in the three-dimensional image in which the virtual stent is placed.

In a case in which the stent cross section 40s overlaps the branch of the blood vessel region 30, the inclination change unit 25 changes the inclination of the stent cross section 40s. In this case, the inclination change unit 25 rotates the stent cross section 40s around an intersection point of the stent cross section 40s and the core line 31, that is, the start position S1 until the stent cross section 40s does not overlap the core line 32 along the maximum contour line of the blood vessel region 30. As a result, the stent cross section 40s does not overlap the branch of the blood vessel region 30 as illustrated in the lower diagram of FIG. 8. Therefore, in the three-dimensional image V1, the stent cross section 40s at the start position S1 is not located at the branch as illustrated in FIG. 9.

The display control unit 26 displays the three-dimensional image V1 as described above or displays various kinds of information required for processes.

Figure 10:
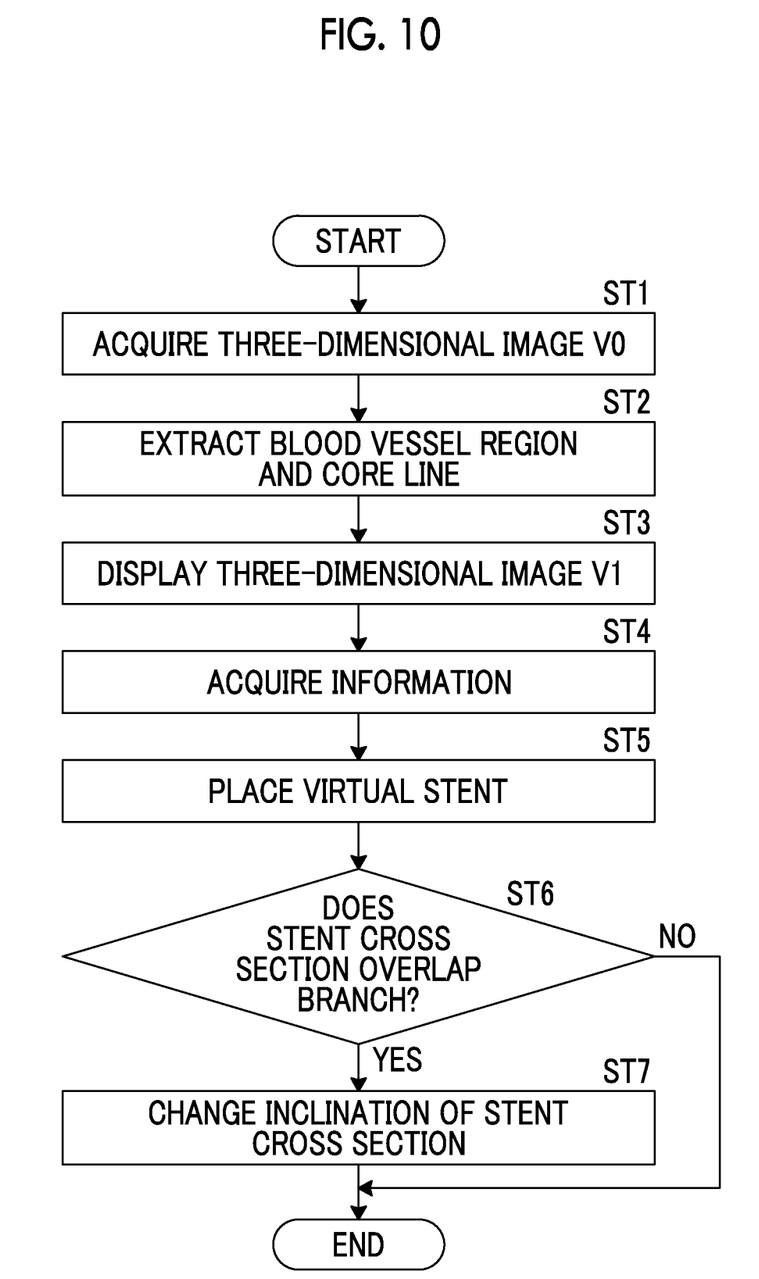
FIG. 10 is a flowchart illustrating a process performed in this embodiment.

Next, the process performed in this embodiment will be described. FIG. 10 is a flowchart illustrating the process performed in this embodiment. First, the image acquisition unit 21 acquires the three-dimensional image V0 (Step ST1). The extraction unit 22 extracts the blood vessel region 30 and the core line 31 of the blood vessel region 30 from the three-dimensional image V0 (Step ST2). In a case in which the core line 32 branched from the core line 31 is present in the three-dimensional image V0, the extraction unit 22 also extracts the core line 32. Then, the display control unit 26 displays the three-dimensional image V1 including the blood vessel region 30 and the core line 31 (Step ST3). The information acquisition unit 23 acquires the information of the diameter of the virtual stent placed in the blood vessel region 30 and the start position S1 and the end position E1 in a case in which the virtual stent is placed (information acquisition; Step ST4). The placement unit 24 places the virtual stent 40 in the blood vessel region 30 (Step ST5). The inclination change unit 25 determines whether or not the stent cross sections 40s and 40e of the virtual stent 40 at the start position S1 and the end position E1 overlap the branches of the blood vessel region 30 (Step ST6).

In a case in which the determination result in Step ST6 is "No", the process ends. In a case in which the determination result in Step ST6 is "Yes", the inclination change unit 25 changes the inclination of the stent cross section with respect to the cross section perpendicular to the core line 31 (Step ST7). Then, the process ends.

As such, in this embodiment, the inclination of the stent cross sections 40s and 40e of the virtual stent 40 placed in the blood vessel region 30 at the start position S1 and the end position E1 with respect to the cross sections Ds and De perpendicular to the core line 31 is changed. Therefore, the inclination of the stent cross sections 40s and 40e are appropriately changed such that the virtual stent 40 does not block the branch of the blood vessel. As a result, in a case in which the stent is actually placed in the blood vessel, it is possible to prevent the stent from blocking the branch of the blood vessel with reference to the position where the virtual stent 40 is placed.

Figure 11:
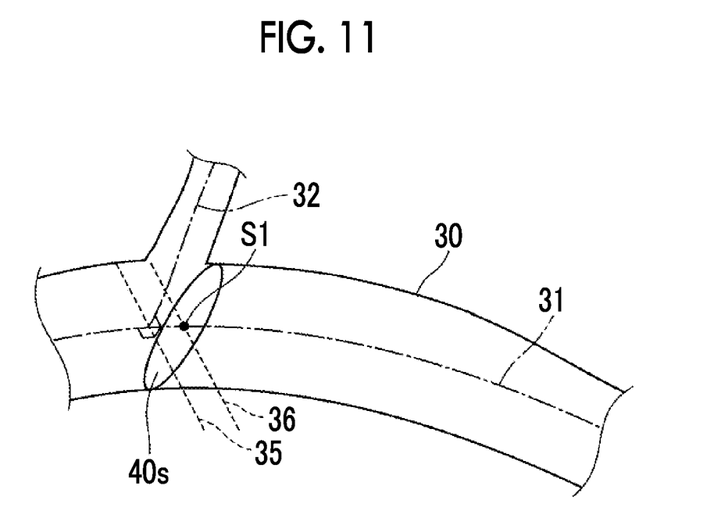
FIG. 11 is a diagram illustrating a change in the inclination of the stent cross section.

In the above-described embodiment, the inclination change unit 25 rotates the stent cross section 40s around the start position S1 along the maximum contour line of the blood vessel region 30. However, as illustrated in FIG. 11, an axis 35 perpendicular to both the core line 31 and the core line 32 may be set, an axis 36 that passes through the start position S1 and is parallel to the axis 35 may be set, and the stent cross section 40s may be rotated on the axis 36 as a rotation axis.

Figure 12:
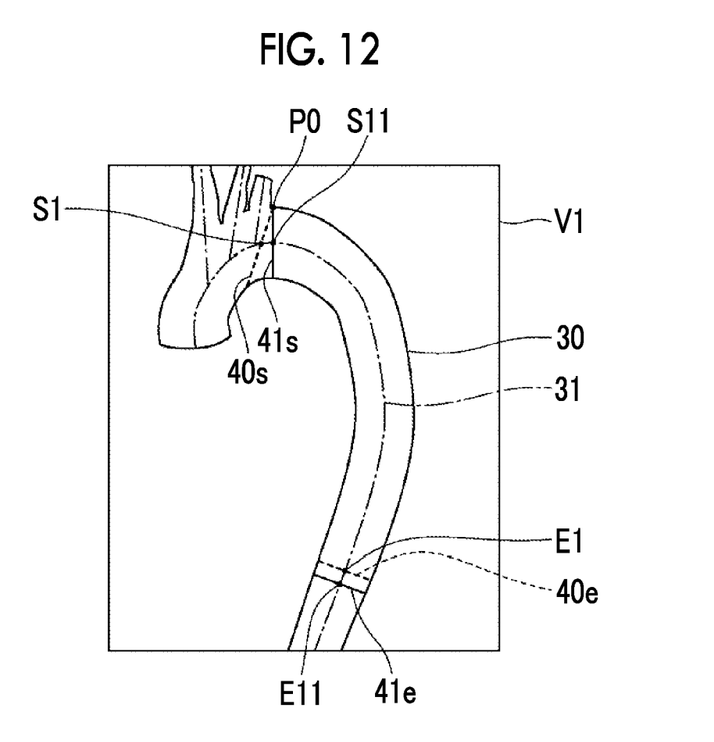
FIG. 12 is a diagram illustrating a change in the position where the virtual stent is placed.

In the above-described embodiment, after the inclination of the stent cross sections 40s and 40e is changed, the placement unit 24 may change the placement position of the virtual stent 40 according to the change in the inclination of the stent cross sections 40s and 40e. FIG. 12 is a diagram illustrating a change in the placement position of the virtual stent. In FIG. 12, the stent cross section 40s whose inclination has been changed as described above is represented by a dashed line. The placement unit 24 calculates an intersection point P0 of the stent cross section 40s whose inclination has been changed and the maximum contour line of the blood vessel region 30. Then, a cross section that passes through the intersection point P0 and is perpendicular to the core line 31 is set as a new stent cross section 41s of the virtual stent at the start position. The new stent cross section 41s intersects the core line 31 at a new start position S11. Since the start position S1 is moved to the new start position S11, the distance between the start position S1 and the new start position S11 may be calculated and the end position E1 may also be moved by the distance to set a new end position E11. A cross section perpendicular to the core line 31 at the new end position E11 is a new stent cross section 41e. In FIG. 12, the mesh pattern of the virtual stent is not illustrated for explanation.

In the above-described embodiment, in a case in which the stent cross sections 40s and 40e overlap the branches of the blood vessel region 30, the inclination change unit 25 changes the inclination of the stent cross sections 40s and 40e until the stent cross section 40s does not overlap the core line 32. However, the inclination change unit 25 may change the inclination of the stent cross sections 40s and 40e in response to a command input by the operator through the input unit 15.

In the above-described embodiment, the aorta is extracted as the blood vessel region 30 from the three-dimensional image V0. However, the blood vessel region 30 is not limited to the aorta as long as the stent needs to be placed in the blood vessel. For example, the coronary artery or the cerebral artery may be extracted as the blood vessel region 30.

In the above-described embodiment, the CT image is used as the medical image.

However, the invention is not limited thereto. For example, an MRI image and a PET image may be used.

EXPLANATION OF REFERENCES

1: virtual stent placement apparatus
2: three-dimensional imaging apparatus
3: image storage server
4: network
11: CPU
12: memory
13: storage
14: display
15: input unit
21: image acquisition unit
22: extraction unit
23: information acquisition unit
24: placement unit
25: inclination change unit
26: display control unit
30: blood vessel region
31, 32: core line
35, 36: axis
40: virtual stent
40s, 40e: stent cross section
41s, 41e: new stent cross section
A1 to A4: line
Ds: cross section at start position
D1, D2: cross section
De: cross section at end position
E1: end position
E11: new end position
S1: start position
S11: new start position
P0: intersection point
V0, V1: three-dimensional image

What is claimed is:

1. A virtual stent placement apparatus comprising:
a non-transitory storage device; and
a processor coupled to the non-transitory storage device and configured to:
  extract a blood vessel region and a core line of the blood vessel region from a medical image;
  acquire information of a diameter of a virtual stent which is placed in the blood vessel region and at least either start position or an end position of the virtual stent in a case in which the virtual stent is placed;
  control to display placing the virtual stent in the blood vessel region;
  control to display changing an inclination of stent cross sections which are cross sections of the virtual stent at least at either the start position or the end position with respect to cross sections perpendicular to the core line;
  control to display a branch of the blood vessel region and the stent cross section at least at either the start position or the end position corresponding to the change of the inclination of stent cross section;
  detect whether the virtual stent overlaps with the branch of the blood vessel region at least by determining whether an extension of a core line of the branch of the blood vessel region intersects with a stent cross section of the stent cross sections; and
  in response to having detected that the stent cross section of the virtual stent overlaps with the branch of the blood vessel region, change the inclination of the stent cross section with respect to the cross section perpendicular to the core line to avoid any intersection between the stent cross section and the extension of the core line of the branch of the blood vessel region by rotating the stent cross section around an intersection point between the stent cross section and the core line of the blood vessel region until the start position of the stent cross section does not overlap the core line of the branch of the blood vessel branch along a maximum contour line of the blood vessel region, wherein the core line is a central line of the branch of the the blood vessel region and is continuous between a start and an end position of the branch of the blood vessel.

2. The virtual stent placement apparatus according to claim 1, wherein the processor is further configured to estimate the diameter of the virtual stent from the blood vessel region.

3. The virtual stent placement apparatus according to claim 1, wherein the processor is further configured to rotates the stent cross section around the start position along a maximum contour line of the blood vessel region.

4. The virtual stent placement apparatus according to claim 3, wherein the processor is further configured to display an axis which is perpendicular to both the core line of blood vessel region and the core line of the branch of the blood vessel region.

5. The virtual stent placement apparatus according to claim 4, wherein the processor is further configured to display another axis which passes through the start position and is parallel to the axis and rotate the stent cross section on the another axis as a rotation axis.

6. The virtual stent placement apparatus according to claim 5, wherein the processor is further configured to change a position according to the start position where the virtual stent is placed with the change in the inclination of the stent cross section.

7. A virtual stent placement method comprising:
extracting a blood vessel region and a core line of the blood vessel region from a medical image;
acquiring information of a diameter of a virtual stent which is placed in the blood vessel region and a start position and an end position of the virtual stent in a case in which the virtual stent is placed;
controlling to display placing the virtual stent in the blood vessel region;
controlling to display changing an inclination of stent cross sections which are cross sections of the virtual stent at least at either the start position or the end position with respect to cross sections perpendicular to the core line;
controlling to display a branch of the blood vessel region and the stent cross section at least at either the start position or the end position corresponding to the change of the inclination of stent cross section;
detecting whether the virtual stent overlaps with the branch of the blood vessel region at least by determining whether an extension of a core line of the branch of the blood vessel region intersects with a stent cross section of the stent cross sections; and
in response to having detected that the stent cross section of the virtual stent overlaps with the branch of the blood vessel region, changing the inclination of the stent cross section which are cross sections of the placed virtual stent at least at either the start position or the end position with respect to the cross section perpendicular to the core line so as to avoid any intersection between the stent cross section and the extension of the core line of the branch of the blood vessel branch by rotating the stent cross section around an intersection point between the stent cross section and the core line of the blood vessel region until the start position of the stent cross section does not overlap the core line of the branch of the blood vessel region, wherein the core line is a central line of the branch of the blood vessel region and is continuous between a start and an end position of the branch of the blood vessel region.

8. A non-transitory computer readable medium storing a virtual stent placement program, wherein execution of the program causes a computer to perform:
extracting a blood vessel region and a core line of the blood vessel region from a medical image;
acquiring information of a diameter of a virtual stent which is placed in the blood vessel region and a start position and an end position in a case in which the virtual stent is placed;
controlling to display placing the virtual stent in the blood vessel region;
controlling to display changing an inclination of stent cross sections which are cross sections of the virtual stent at least at either the start position or the end position with respect to cross sections perpendicular to the core line;
controlling to display a branch of the blood vessel region and the stent cross section at least at either the start position or the end position corresponding to the change of the inclination of stent cross section;
detecting whether the virtual stent overlaps with the branch of the blood vessel region at least by determining whether an extension of a core line of the branch of the blood vessel region intersects with a stent cross section of the stent cross sections; and
in response to having detected that the stent cross section of the virtual stent overlaps with the branch of the blood vessel region, changing the inclination of the stent cross section which are cross sections of the placed virtual stent either at the start position or the end position with respect to the cross section perpendicular to the core line so as to avoid any intersection between the stent cross section and the extension of the core line of the branch of the blood vessel region by rotating the stent cross section around an intersection point between the stent cross section and the core line of the branch of the blood vessel region until the start position of the stent cross section does not overlap the core line of the branch of the blood vessel region, wherein the core line is a central line of the blood vessel branch and is continuous between the start position and the end position of the branch of the blood vessel region.

* * * * *